Figure 1:
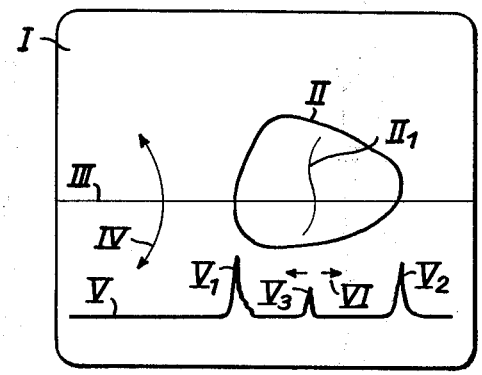

United States Patent [19]

Baumgartner

[11] 4,010,634

[45] Mar. 8, 1977

[54] ULTRASONIC INSPECTION METHOD

[75] Inventor: Franz Baumgartner, Zipf, Austria

[73] Assignee: Kretztechnik Gesellschaft m.b.H., Zipf, Austria

[22] Filed: Oct. 28, 1975

[21] Appl. No.: 626,066

[30] Foreign Application Priority Data

Nov. 6, 1974 Austria ............................ 8911/74

[52] U.S. Cl. ........................ 73/67.8 S; 128/2 V; 128/2.05 Z
[51] Int. Cl.$^2$ ...................................... G01N 29/00
[58] Field of Search .......... 73/67.8 R, 67.8 S, 67.7; 128/2 V, 2.05 Z; 340/324 AD, 5 MP, 5 R

[56] References Cited

UNITED STATES PATENTS 3,159,023   12/1964   Steinbrecher ................... 128/2 V
3,621,708   11/1971   Regas .............................. 73/67.8 S

OTHER PUBLICATIONS

Kikuchi et al., Journal of Acoustical Society of America, "Early Cancer Diagnosis Through Ultrasonics", vol. 29, No. 7, pp. 824–833, July 1957.

Metrix Incorporated Publication, "Echo Scan and Echo Trace Ultrasonic Analyzers", pp. 1–4, 1965.

Kossoff et al., Ultrasonics, "Design Criteria for Ultrasonic Visualization Systems", Jan.–Mar. 1964, pp. 29–38.

Primary Examiner—Richard C. Queisser
Assistant Examiner—Stephen A. Kreitman
Attorney, Agent, or Firm—Kurt Kelman

[57] ABSTRACT

An ultrasonic sound beam is caused to penetrate an object to be inspected and is moved in a scanning plane of the object transversely to the axis of the beam. A B-scan display of the object is displayed on a display screen in response to echo pulses produced by the object under the action of the sound beam moving in the plane. An adjustable trace is defined on the display screen at a location which corresponds to a predetermined position of the sound beam during the movement thereof in the plane. A display other than the B-scan display is derived from echo pulses produced by said object under the action of said sound beam when the same is in said predetermined position.

15 Claims, 2 Drawing Figures

U.S. Patent

Mar. 8, 1977

4,010,634

ULTRASONIC INSPECTION METHOD

This invention relates to a method of inspecting objects with ultrasonics, in which a B-scan display is produced on a display screen by a sound beam transmitted into an object and moved transversely to its own axis, the plane of the display being determined by the direction of movement and the axis of the sound beam, and the echo pulses received when the sound beam has preselectable directions are displayed in a mode which differs from the B-scan display, particularly as a time-motion display or an A-display.

The invention relates also to apparatus for carrying out the method, comprising an ultrasonic inspecting device which comprises a display screen, a scanning mechanism or the like for moving a sound transducer or a sound beam in a predetermined or preselectable plane, and control means which selectively cause the signals received by the sound transducer to be displayed in the form of a B-scan display or in another display mode.

In an inspection of objects with ultrasonics it is sometimes desirable or even necessary to display a B-scan and to inspect the same object or a predetermined part thereof also by another ultrasonic inspection method for a reliable evaluation. By way of example, an inspection of the heart may be referred to. A B-scan can be displayed to represent the position and shape of the heart but in this case the heart can normally be displayed only in a stationary state so that only rough indications, at best, are available as regards its motion. For an exact indication of this motion, an inspection by the time-motion method is required, in which the motion is displayed by a curve as a function of time. In other cases, an A-display will be recommendable so that the motion of only a specific part of the heart, e.g., of a cardiac valve, is displayed and/or recorded. A significant disadvantage involved in the time-motion method resides in that the path of the sound beam through the specimen being inspected is not directly indicated and it is not ensured that the echo which is recorded actually comes from the interesting part of the object.

B-scan display apparatus are known in which the sound beam is moved only slowly in a direction that is transverse to its axis so that a slow scanning is performed and the signals (echoes) received from the scanning plane of the object during the several phases of the motion of the sound transducer or sound beam are stored and utilized to display the B-scan on the display screen. In such apparatus the sound beam can be passed through the object in an exactly predetermined direction. A complete B-scan is displayed first and the object is then scanned once more with the slowly moved sound beam so that bright dots light up within the B-scan display. The location of each of said dots indicates the instantaneous direction of the sound beam in the object. When the sound beam has reached the desired position, the sound transducer is fixed in the resulting position and the apparatus is switched over to the other display mode so that the signals received during the display in said other mode can be associated with a predetermined direction of the sound beam. During a normal, slow scanning of an object for the display of a B-scan, it is not possible properly to display a moving object and the B-scan displays of moving objects are blurred owing to the motion of the object because the reflecting points in the object which ought to be displayed by dots in the B-scan display are in fact displayed by lines as a result of the motion. The result is similar to photographs taken of objects moving at high speed with a stationary camera and a long exposure time. For the reasons set forth, the method which has been described is used only for an inspection of stationary objects for which a time-motion inspection is not interesting, and only a change from the B-scan display to the other display mode is possible and useful, i.e., the B-scan display and the A-display can be shown individually rather than combined.

German Patent No. 1,258,015 discloses a method which serves to produce sharp B-scan displays of periodically moving objects in spite of slow scanning. In that method, the B-scan display is composed of numerous component images, each of which is received only for a very short time, and a synchronizer is provided which ensures that each component image is received during a predetermined phase of the motion of the object. That process is very slow because the object must perform a large number of motions until a complete B-scan has been displayed. Besides, the resulting display shows the moving object at rest in a predetermined phase of its motion so that the motion itself cannot be monitored directly on the B-scan display.

When it is desired to display also a motion of the object in the B-scan, a very fast scanning is required so that the time required to display a complete image is short relative to the duration of one cycle of motion of the object. Such fast scanning is possible either by the use of motor-driven sound transducers or by the use of multiple sound transducers and electronic switching means for enabling the individual sound transducers in succession to cause the sound beam to perform the required transverse movement in the object. In the latter case the sound beam moves step by step from each sound transducer to the next. Such multiple sound transducers are not and cannot be used with means for a temporary storage and the display screens must have in this case only a short persistence time because the images which appear in succession on the display screen and which can readily display the object in different phases of motion differ from each other and for this reason must not be projected one over the other as this would result in blurred images. For this reason it is not possible in the methods described to select a predetermined direction of the sound beam in view of the information obtained from the image itself or during a slow second scanning, as is known from the static method, and then to change over to the other display mode. During the normal display of the B-scan, the dots of the image move over the display screen so fast that the viewer cannot recognize their location and the dots appear to him as a bright line. If the sound beam were moved more slowly, the B-scan display would immediately disappear from the display screen because only a short persistance time is permissible, and the viewer would again lack an indication of the position of the sound beam in the object.

In a method of the kind defined first hereinbefore, the improvement provided by the invention resides essentially in that the sound beam is moved in known manner transversely to its axis at a velocity which is sufficient to produce an instantaneous B-scan display of a moving object and preferably in a reciprocating motion, an adjustable trace line, which corresponds to at least one intermediate position assumed by the sound beam during each stroke, is defined in the B-scan display, and the signals received at the time when the position of the sound beam corresponds to the displayed trace line are selectively represented in the other display mode.

In carrying out the method according to the invention, it is possible to select in the displayed B-scan a predetermined direction of the sound beam and to display the signals received when the sound beam has said direction in the other display mode so that it is possible to exactly predetermine a part of the inspected object which is to be inspected with the other display mode.

Because the possible directions of the sound beam are definitely associated with individual scanning lines of the image, the trace line may be constituted in the simplest case by a pointer which is mechanically movable over the display screen, i.e., of a mechanical member, which is movable in a limited range that is defined so that the pointer can assume on the display screen only positions which correspond to respective scanning lines. It is preferable, however, to use the writing beam itself for a display of the trace line on the display screen. The information representing the adjustment or the adjusted location of the trace line may be directly used to derive the signals for the other display mode.

In practice the method according to the invention may be used in various ways. In apparatus which enables a display only in one mode at a time, it will be preferable to stop the sound beam when it reaches the position defined by the displayed trace line and to effect the change from the B-scan display to the display in the other mode at the same time so that any desired time is then available for the inspection of the display in the other mode. Alternatively, the result of the inspection may be displayed in both display modes at the same time and preferably in different regions of one and the same display screen so that the results of the inspection are even more clearly apparent. In the latter case, a preselector circuit may be provided by which the signals produced by the sound beam at the trace line are fed to the switching means which cause a display in the other mode. In this case, a gate may be provided which causes one or more scanning lines to be blanked in the B-scan display — these blanked lines represent the trace line — or the trace line may be added, e.g., by the gating of a bright line, whereas the signals received from the region corresponding to the trace line are displayed simultaneously in the same scanning line of the B-scan display and in the other display mode. For the other display mode, time-controlled gating circuits may be used to effect a display only of interesting portions of the trace line in the other mode; these portions may be indicated in the B-scan display by marks which are adjustable along the trace line.

The method according to the invention is preferably carried out with apparatus which is of the kind defined hereinbefore and which comprises, in accordance with the invention, means for defining on the display screen a trace line which appears on the display screen together with the B-scan display at a location which corresponds to a position adapted to be assumed by the sound beam in the inspected object and which is adjustable in at least part of the B-scan display, and a mechanical or electronic preselector switch associated with the control means for switching to the other display mode, which preselector switch is adapted to be preadjusted in unison with the trace line so that said control means effect a change to the other display mode when the trace line displayed in the B-scan display represents the actual positions of the sound beam in the object.

Figure 2:
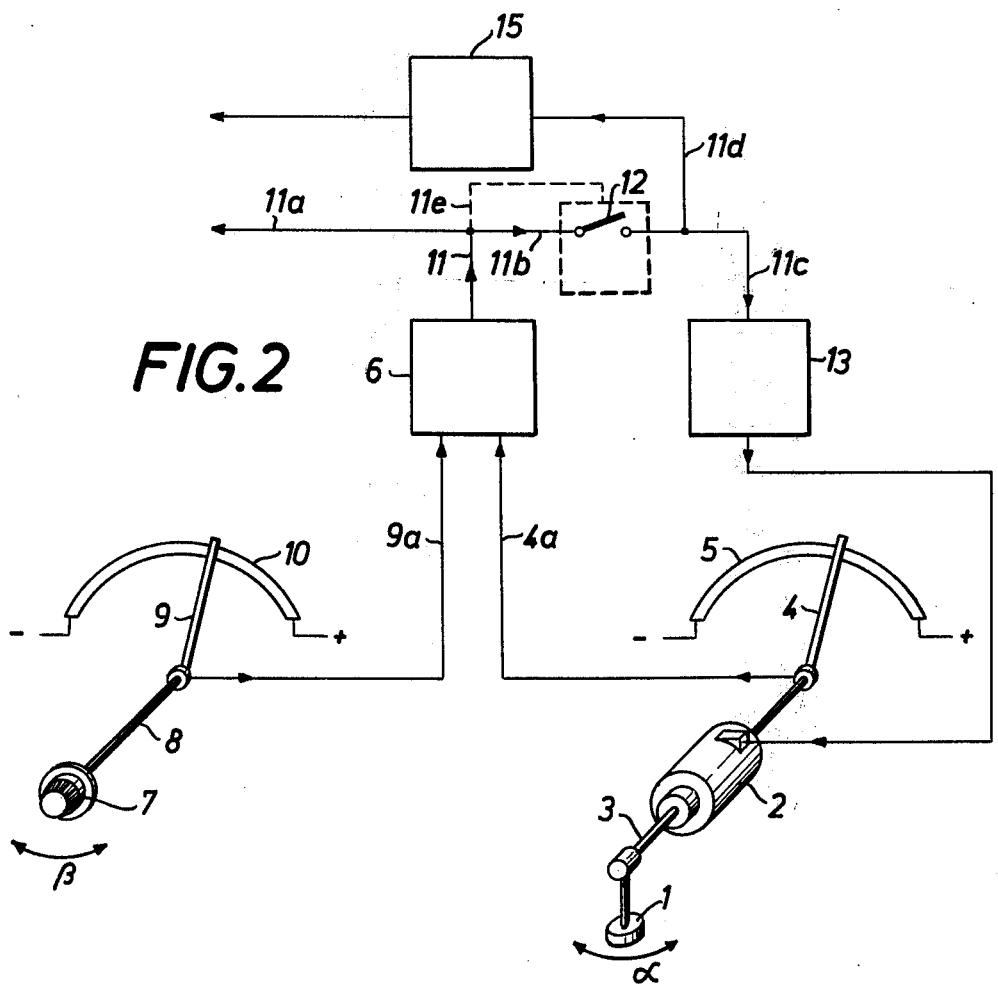

An embodiment of the invention is illustrated by way of example on the accompanying drawing, in which FIG. 1 is a highly diagrammatic view showing the display screen of an ultrasonic inspection apparatus during an inspection of the heart, and FIG. 2 is a basic circuit diagram showing control means which may be added to a conventional B-scan display apparatus so that the same can be used to carry out the method according to the invention.

The embodiment shown by way of example comprises a B-scan display apparatus in which the sound transducer is driven by a scanning mechanism to perform fast periodic pivotal movements so that the sound beam emitted by the sound transducer traverses the object at a given time in a scanning plane defined by the axis of the sound beam and its pivotal movement. At any given time, the object is inspected in a sector which is defined by the range of movement of the sound transducer. Electric signals are derived from the movement of the sound transducer and are applied to the deflecting plates of a cathode ray tube, which comprises a display screen I. The signals applied to the deflector plates result in a deflection of the electrode beam so that the line scanned by the electrode beam on the display screen at any given time corresponds to the instantaneous position of the sound beam in the inspected object. This results in the display of a B-scan display II on the display screen I shown in FIG. 1. The brightness of the B-scan display is so adjusted that the base line is only slightly visible or is not visible at all. In response to the signals (echoes) received by the sound transducer, short bright-up pulses are produced so that dots appear on the display screen along paths which correspond to the locations of the reflecting faces in the inspected object. Because the motion is very fast and is periodically repeated, the individual dots cannot be recognized as such but only the paths described by them are apparent and the impression of a complete B-scan display II is produced. In the embodiment shown by way of example in FIG. 1, a B-scan display of a heart is diagrammatically indicated by its contour line. As far as the method and the B-scan display apparatus used to carry out the method have been described thus far, they are basically known.

In accordance with the invention, a trace line III is displayed on the display screen I of the embodiment shown in FIG. 1. This trace line III consists, for instance of a gated bright scanning line and is adjustable in the direction of arrow IV and extends on the display screen in a direction which represents a possible direction of the sound beam in the object. When the sound beam reaches in the object the position which is represented by the trace line III, the received signals are utilized to display the result of the inspection in another mode. An A-display is shown by way of example in FIG. 1. In the trace V, $V_1$ represents the echo or the front wall of the heart, $V_2$ the echo of the rear wall of the heart, and $V_3$ the echo of a cardiac valve $II_1$ moving strongly in the direction of arrow VI. Instead of an A-display, a time-motion display of the motion of the cardiac valve may be obtained on the display screen. In this case the horizontal sweep will be very slow so that a plurality of cardiac cycles can be displayed at a time, whereas the deflection in a vertical direction will correspond to the amplitude of motion of the echo $V_3$. The region to be represented in the time-motion mode may be exactly defined by limiting marks, which are provided on the trace line III and adjustable along the same and which are associated in known manner with gating circuits which ensure that only echoes within the range defined by these marks are utilized for the additional display.

The means which are essential in a B-scan display apparatus or must be added thereto for carrying out the method according to the invention are shown in FIG. 2. A sound transducer 1 is connected by a shaft 3 to a gearmotor 2 and is driven by the gearmotor 2 to perform a pivotal movement through an angle $\alpha$ in a preselected scanning plane. The velocity of the transverse movement resulting from the pivotal movement is high relative to the movement of the inspected object itself so that the instantaneous position of the object can be displayed in different phases of its motion. For an inspection of the heart, the angle $\alpha$ may amount to, e.g., 60°. The sound transducer 1 is pivotally moved at such a velocity that about 30 milliseconds are required for its movement through said angle and for a formation of a B-scan display. The shaft 3 carries a wiper 4 of a potentiometer 5 so that the wiper 4 performs a pivotal movement in unison with the transducer 3 and the voltage applied to the wiper is a measure of the instantaneous angular position. This voltage is applied by a line 4a to a comparator 6.

For adjusting trace line III shown in FIG. 1, the circuit shown in FIG. 2 comprises a setting member 7 which is adjustable, e.g., by hand and by means of a shaft 8 adjusts a wiper 9 of another potentiometer 10. Each angle $\beta$ to which the setting member 7 can be adjusted corresponds to an angle which is smaller than the angle $\alpha$ through which transducer 1 is movable. The voltage applied to the wiper 9 is fed through a line 9a to the comparator 6. This comparator 6 is arranged to deliver a pulse to a line 11 when the voltages applied to the two potentiometers 5, 10 are equal. This pulse is transmitted by line 11a and used to control the brightness of the cathode ray tube and thus to produce trace line III. Said pulse is preferably not used directly for producing the trace but is applied to a monostable multivibrator, not shown, which produces a rectangular pulse having a predetermined duration and used to produce the trace. As a result, the duration of the pulse is independent of the velocity of the sound transducer 1 and may be adjusted to be exactly equal to the duration of a sweep cycle of a sweep generator in the ultrasonic apparatus. As a result, a scanning line or base line at the B-scan display is brightened once throughout its length whenever the sound transducer 1 moves through a position which has been preselected by means of the setting member 7 and the potentiometer 10. The trace line III appearing on the display screen indicates in the B-scan display the position assumed by the sound beam in the inspected object at the time at which the bright trace line appears. Because this phenomenon is repeated in rapid succession, it results in the visual impression of a continuous display of a trace line in the B-scan display.

The trace line scanning means 6–11 do not only enable a shifting of the trace line and of the selected position of the sound beam during an inspection but serve also to preselect that portion of the object which is to be displayed in another mode for the inspection. If in the circuit shown in FIG. 2 a switch 12 in a branch line 11b connected to the line 11 is closed, the pulse delivered by the comparator will be applied through line 11c to a switch unit 13 and through a line 11d to a mode-changing switch 15. The switch unit 13 causes the gearmotor 2 to stop so that the sound transducer 1 is held in the position which has been preselected by the setting of the trace line III. Thereafter, the sound transducer delivers pulses only in the line which corresponds to the trace line. The mode-changing switch 15 switches the display screen to the other display mode so that only trace V, for example, appears on the display screen.

The operation of the arrangement shown in FIG. 2 will now be summarized. As long as the switch 12 is open, the normal B-scan display II and the superimposed line III appear on the display screen I of the apparatus. The location of this trace line can be varied by means of the setting member 7. When the desired location has been set and the switch 12 is closed, the sound transducer 1 moves until the sound beam emitted by it assumes the desired position represented by the trace line on the display screen. At that time the sound transducer is stopped and the apparatus is changed to another display mode so that the B-scan display disappears and the display in the other mode appears.

The circuit arrangement which has been described may be modified in that the switch 12 is replaced by an electronic switch and the line 11c and the switch unit 13 are omitted. The electronic switch is controlled by the comparator 6 via line 11e and in response to the pulse delivered by the comparator 6 is closed for a preselected time, which is short compared to the time required for a stroke of the sound transducer. As a result, the apparatus is switched to the other display mode only for the time in which the electronic switch is closed. As is shown in FIG. 1, the B-scan display and the display in the other mode can appear on the display screen I at the same time. The trace line III need not be displayed but may appear in the B-scan display as a blanked scanning or group of scanning lines. The motion of the sound transducer is not interrupted and the B-scan display remains visible also during the display in the second mode. The display in the second mode is normally constituted by a series of dots rather than by a continuous line. If the sound transducer moves at sufficiently high velocity, the dots will appear in such a close succession that the result sufficiently exactly displayed also in the second mode.

If the sweep frequency of the B-scan display apparatus can be varied to vary the range of measurement, the multivibrator for producing the pulse for the trace line may be controlled in dependence on the sweep frequency so that the duration of this pulse always equals the duration of the sweep cycle and a bright base line appears on the display screen whenever the sound beam reaches the selected position; this base line becomes visible as trace line III throughout its length.

The method according to the invention may also be adopted if the motion of the sound beam differs from the pivotal movement described with reference to FIG. 1 and is produced by different means. For instance, the sound transducer may be reciprocated along a straight line or multiple sound transducers comprising electronically switched individual transducers may be used. The potentiometers 5, 10 may be replaced by different pick-ups or by preselector switches for indicating the position of the sound transducer and controlling the location of the trace line. For instance, inductive or capacitive pick-ups may be used. It will be understood that the method is not restricted to the medical inspections which have been described but may also be adopted for technical inspections.

What is claimed is:

1. A method of inspecting a moving object, which comprises the steps of
   1. transmitting an ultrasonic sound beam into the moving object and moving the sound beam in a scanning plane transversely to the axis of the sound beam, the scanning plane being defined by the moving sound beam axis and the sound beam being moved in the scanning plane at a velocity sufficient for an instantaneous B-scan display of the moving object,
   2. displaying the B-scan on a display screen in response to echo pulses produced in the scanning plane by the ultrasonic sound beam in the moving object,
   3. producing an adjustable trace line in the B-scan display at a location which corresponds to a predetermined position of the sound beam during the movement thereof in the scanning plane, and
   4. selectively displaying on the display screen a display other than the B-scan display in response to echo pulses produced when the sound beam is in the predetermined position.

2. The inspecting method of claim 1, wherein the sound beam is moved back and forth in the scanning plane.

3. The inspecting method of claim 1, wherein the other display is a time-motion display.

4. The inspecting method of claim 1, wherein the other display is an A-display.

5. The inspecting method of claim 1, wherein the movement of the sound beam is stopped in the predetermined position.

6. The inspecting method of claim 1, wherein the B-scan display and the other display are displayed simultaneously.

7. The inspecting method of claim 6, wherein the displays are simultaneously displayed on different locations of the display screen.

8. An apparatus for inspecting a moving object, which comprises
   1. an ultrasonic sound transducer for emitting an ultrasonic sound beam and transmitting the sound beam into the moving object,
   2. scanning means for moving the sound beam in a scanning plane transversely to the axis of the sound beam, the scanning plane being defined by the moving sound beam axis and the scanning means being arranged to move the sound beam in the scanning plane at a velocity sufficient for an instantaneous B-scan display of the moving object,
   3. a display screen operatively connected to the scanning means for displaying the B-scan in response to echo pulses produced in the scanning plane by the ultrasonic sound beam in the moving object,
   4. means for producing a trace line in the B-scan display and for adjusting the location of the trace line to one which corresponds to a predetermined position of the sound beam during the movement thereof in the scanning plane,
   5. a control for selectively displaying on the display screen a display other than the B-scan display in response to echo pulses produced when the sound beam is in the predetermined position, and
   6. a preselector switching means settable to switch from the B-scan to the other display when the direction of the trace line in the B-scan display corresponds to that of the sound beam in the moving object.

9. The inspecting apparatus of claim 8, wherein the switching means includes a mechanical switch.

10. The inspecting apparatus of claim 8, wherein the switching means includes an electronic switch.

11. The inspecting apparatus of claim 8, further comprising a separately operable switch connected between the scanning means and the switching means.

12. The inspecting apparatus of claim 8, wherein the scanning means comprises a switch for stopping the movement of the sound beam in response to the operation of the preselector switching means switching from the B-scan to the other display.

13. The inspecting apparatus of claim 8, wherein the control comprises a comparator having a first input arranged to receive first electric signals representing the instantaneous position of the sound beam and adapted to be displayed on the display screen as dots in response to signals received from the moving object, and a second input arranged to receive second electric signals controlled by the preselector switching means and representing the direction of the trace line, the comparator being arranged to detect a predetermined relation of the first to the second electric signals when the sound beam is in the predetermined position, and the preselector switching means being operated in response to the predetermined relation by the comparator.

14. The inspecting apparatus of claim 13, wherein the electric signals are voltage signals.

15. The inspecting apparatus of claim 8, wherein the trace lines is a bright scanning line.

* * * * *